United States Patent [19]

Breaux et al.

[11] 4,026,955
[45] May 31, 1977

[54] PREPARATION OF PENTACHLORONITROBENZENE

[75] Inventors: Paul W. Breaux, Cleveland; Wendell D. Newman, Delano; Philip E. Quinnett, Cleveland, all of Tenn.

[73] Assignee: Olin Corporation, New Haven, Conn.

[22] Filed: May 4, 1976

[21] Appl. No.: 683,437

[52] U.S. Cl. .................. 260/646; 260/703
[51] Int. Cl.$^2$ ........................ C07C 79/12
[58] Field of Search ............. 260/646, 703

[56] References Cited
UNITED STATES PATENTS 3,026,358  3/1962  Lojewski ............ 260/646
3,984,487  10/1976  Watts et al. ............ 260/646

FOREIGN PATENTS OR APPLICATIONS 711,738  6/1965  Canada ............ 260/646

Primary Examiner—Leland A. Sebastian
Attorney, Agent, or Firm—William A. Simons; Thomas P. O'Day; F. A. Iskander

[57] ABSTRACT

Pentachloronitrobenzene having less than 0.6% hexachlorobenzene is prepared by reacting pentachlorobenzene with mixed nitration acid at a temperature in the range of 100°–120° C then heating the reaction mixture to an intermediate temperature to deplete excess nitric acid prior to melting and recrystallization.

7 Claims, No Drawings

PREPARATION OF PENTACHLORONITROBENZENE

BACKGROUND (1). Field of Invention

The present invention relates to a process for preparing pentachloronitrobenzene. More particularly the invention relates to a process for producing pentachloronitrobenzene having unexpectedly reduced levels of hexachlorobenzene while simultaneously avoiding excess contamination with pentachlorobenzene.

(2). Prior Art

Pentachloronitrobenzene is a commercially important fungicide for application to soil and seeds for controlling various plant diseases. It is particularly effective in controlling plant diseases caused by botrytis, fusarium, rhizoctonia and anthracnase.

Several methods are known for preparation of this compound. Those of significance to the process described herein involve nitration of pentachlorobenzene with mixed nitration acid which, as used herein, consists essentially of a mixture of nitric and sulfuric acids.

Canadian Patent No. 620,338 discloses one such process wherein 50–90% of the pentachlorobenzene is added to preheated (80°– 90° C) mixed nitration acid while maintaining the resulting temperature in th range of 90° to 95° C. The remaining pentachloronitro benzene is then added while maintaining a temperature of 90°–100° C following which the temperature is raised and held at 120° to 130° C to complete the reaction. The reaction mixture is then cooled and product recovered. As best seen from Example 3 of the patent, the resulting product (after removal of sulfuric acid, nitric acid and water) contains about 1% pentachlorobenzene and about 2.1% hexachlorobenzene. Industry standards require that these impurity levels be reduced substantially. This is clearly not attained utilizing the temperature control scheme set forth in this patent.

Pentachloronitrobenzene has been prepared commercially utilizing mixed nitration acid by adding excess mixed nitration acid to pentachlorobenzene at a rate sufficient to maintain a reaction temperature in the range of 120°–135° C. The resulting product at this point in the process is a slurry of undesirably fine pentachloronitrobenzene crystals which may contain unacceptable levels of pentachlorobenzene. To improve crystal characteristics and deplete pentachlorobenzene, the slurry is then rapidly heated to above the melt point (142°–144° C) of the pentachloronitrobenzene, and then cooled to recrystallize pentachloronitrobenzene. While the pentachloronitrobenzene thus produced contains minimal amounts of pentachlorobenzene, it still contains about 1–1.5% hexachlorobenzene, a commercially unacceptable level. This process has also been practiced using an initial reaction temperature of about 105°–110° C with a rapid heat up cycle following acid addition as in the commercial process. Little, if any, reduction in hexachlorobenzene content was noted. The reaction has also been run at an addition temperature of 140°–145° C producing a pentachloronitrobenzene product containing from 1–1.9 percent hexachlorobenzene. Jackson et. al., *J. Org. Chem.* 36 (23) 3638-9 (1971).

Considerable research effort has ben expended to find means for nitrating pentachlorobenzene with mixed nitration acid to produce pentachloronitrobenzene in yields exceeding about 98% while simultaneously obtaining a product having a hexachlorobenzene content of not more than about 0.6%.

We have now found that there is a critical relationship between hexachlorobenzene formation and the precise addition and post-addition reaction parameters utilized; and further that, in order to meet the requirements set forth above, several conditions must be met. A low initial reaction temperature during the addition must be utilized. Following the low temperature addition period the resulting reaction mixture must be heated to an intermediate temperature range to complete the reaction and must then be held in this range for a period of time sufficient to deplete the nitric acid concentration to a predetermined value. Thereafter the mixture may be heated above the melt temperature and then cooled to recrystallize pentachloronitrobenzene in high yields, having excellent crystal characteristics and having a low hexachlorobenzene content.

SUMMARY OF THE INVENTION

In accordance with these findings there is provided a process for preparing pentachloronitrobenzene having a hexachlorobenzene content of not more than 0.6% by weight comprising generally the steps of:

1. Mixing together at an initial reaction temperature in the range of 100°–120° C pentachlorobenzene and a mixed nitration acid providing a molar excess of nitric acid, 2. Heating the resulting reaction mixture to an intermediate temperature in the range of 130° C up to the melt point and maintaining the reaction mixture in said intermediate range for a time sufficient to deplete the nitric acid concentration thereof to a value of not more than 1% by weight based on the weight of the liquid fraction of the resulting slurry, 3. Thereafter heating the resulting slurry to a temperature in the range of 142° to 160° C to form a melt and then cooling the melt to recrystallize pentachloronitrobenzene containing not more than 0.6% hexachlorobenzene.

DETAILED DESCRIPTION

The substrate for the present reaction is pentachlorobenzene which is prepared commercially by halogenating benzene, mono-, di-, tri- or tetra-chlorobenzene or mixtures of any of these and recovering pentachlorobenzene by known means, for example by distillation. In accordance with known methods, the pentachlorobenzene recovered is substantially free of hexachlorobenzene. It is important that the starting material be substantially free of hexachlorobenzene since, even under the conditions set forth herein, some hexachlorobenzene will be formed during the nitration.

The mechanism of hexachlorobenzene formation in the nitration of pentachlorobenzene is still not fully understood. Jackson et. al., supra, postulated that it occurred by attack of some polar reagent generated in situ or nitric acid itself on pentachlorobenzene. If this were true, formation of hexachlorobenzene would be expected to occur in the early stages of the reaction when there is substantial amounts of pentachlorobenzene available for reaction. We have found, however, that hexachlorobenzene is not formed to any significant degree during the early low temperature stage of the reaction. To the contrary, we have found that formation of hexachlorobenzene is a temperature related phenomenon which occurs for the most part in the terminal stages of the reaction as temperature is increased toward the melt temperature and at a time when very little pentachlorobenzene is present in the reaction mixture. According to our studies, a dramatic increase in hexachlorobenzene formation occurs in a mixed acid system at or above a temperature of about 138°–142° C. We have also found that when nitric acid is depleted to a value of 1% by weight or less of the liquid fraction of the slurry prior to raising the temperature above the melt point, the rate of hexachlorobenzene formation undergoes a dramatic decrease during subsequent melt cycle.

The nitrating agent is mixed nitration acid which, as indicated above, consists essentially of sulfuric and nitric acid. While it is not believed to be critical, it is advantageous to employ a mixed acid having a nitric acid content of from 12.5 to about 25%, preferably 15–20% by weight nitric acid to assure the presence of sufficient sulfuric acid to take up the water formed during the reaction. Sulfur trioxide may also be added (as in commercial oleum) if desired.

Sufficient mixed nitration acid is utilized to provide an excess of nitric acid. At least a 25% molar excess should be employed to assure consistent high conversion. Advantageously, a 40 to 100% excess is utilized with a 50–75% excess being preferred. Thus sufficient mixed acid is utilized to provide 1.25–2, advantageously 1.4–2, and preferably 1.5–1.75 moles of nitric acid per mole of pentachlorobenzene.

The reaction is conducted by mixing together pentachlorobenzene and the mixed nitration acid by adding one to the other at a rate sufficient to maintain a selected initial reaction temperature. It is not believed critical whether the pentachlorobenzene is added to the mixed acid or vice versa as long as proper temperature control is maintained during the addition period. For the purpose of simplicity the process will, however, be described assuming mixed acid addition to pentachlorobenzene.

The reaction between pentachlorobenzene and mixed nitration acid is highly exothermic. In order to control the temperature of the reaction mixture during addition, it is necessary to add the acid (or the pentachlorobenzene) at a rate sufficient to control the temperature to within the desired initial temperature range. If external cooling is provided more rapid addition may be utilized but such cooling is not essential. It is essential to proper temperature control that the reactants be well mixed together throughout the addition by known stirring or agitation means.

In accordance with the present invention, the addition is made at a rate sufficient to maintain the reaction mixture at a temperature in the range of 100°–120° C, preferably 105°–115° C. At temperatures below about 100° C, several production problems are encountered involving difficult temperature control, excess viscosity and inadequate production rates. At an initial reaction temperature above 120° C, the rate of hexachlorobenzene formation is sufficiently rapid that the reaction cannot be conducted without forming excess quantities of hexachlorobenzene. Accordingly, it is necessary to conduct the addition at a temperature within the specified range. At this temperature, the reaction proceeds, depending on the precise temperature utilized, to about 80–95% completion without significant formation of hexachlorobenzene.

The reaction mixture is then heated at any desired rate to an intermediate temperature in the range of 130° C up to the melt point, approximately 142°–144° C, advantageously 130°–140° C, preferably 132°–138° C, and maintained in this range for a period of time sufficient to deplete the nitric acid concentration thereof to a value of not more than 1%, preferably not more than 0.8% by weight of the liquid fraction of the resulting slurry. The reduction to this level must be effected prior to reaching the melt point of pentachloronitrobenzene and is preferably attained prior to exceeding 138° C in order to assure adequate temperature control in the system.

The preferred method for effecting the nitric acid depletion is to heat slowly through the rate at a predetermined rate which will effect depletion before the critical temperature is reached. The predetermined rate must take into account the amount of nitric acid present. Therefore, the heating rate will decrease where a larger amount of nitric acid is present and will increase where smaller amounts are present. To minimize the time period during which the temperature must be held within this range, it is preferable to utilize only that excess of nitric acid which is required to consistently complete conversion for a given temperature profile. Use of larger excesses necessitates the use of higher temperatures within the range and/or greater time of exposure at the intermediate temperature level in order to effect the required depletion. This in turn increases the likelihood that additional hexachlorobenzene formation will occur as its formation is a function of both time and temperature.

If the depletion is effected as indicated above, i.e., by heating at a substantially constant rate through the intermediate temperature range, a temperature profile which increases reaction mixture temperature by about 8°–18° C, preferably 10°–15° C per hour is advantageously employed. On the other hand, the same result may be obtained by heating rapidly to a predetermined temperature in the specified range and holding at that temperature until the desired degree of depletion is effected. As claimed, the invention embodies either of these modes of operation as well as other minor variations thereof.

As indicated above, the nitric acid level is reduced to below 1% and preferably below 0.8% of the liquid fraction of the slurry produced during the intermediate temperature cycle. For purposes of the present invention, the nitric acid level is most conveniently measured for any given system at any given point in time by removing a sample, separating the solids, dissolving 5 g of filtrate in 50 ml sulfuric acid and diluting with additional sulfuric acid to 100 ml, titrating with a standardized solution of ferrous sulfate to a persistent brown endpoint, then calculating the nitric acid value as a weight percent of the filtrate.

This method for determining when adequate depletion has taken place is, however, only utilized to establish the time/temperature relationship for any given system. It is understood that once the desired levels are attained for that system the reaction will most preferably be controlled by controlling the nitric acid content of the starting mixed acid, controlling the ratios of starting mixed acid to pentachlorobenzene and then establishing a time/temperature profile for the system such that the desired nitric acid levels will be attained prior to heat up for the melt cycle.

Following depletion of nitric acid to the required level, the reaction mixture is then heated to a temperature above the melt temperature of the crystallized solids (generally about 142°–144° C) and held at this temperature for a period of time sufficient to provide a liquid melt. For this purpose, temperatures in the range of 142° C to 160° C, preferably 145°-155° C are utilized. Hold time will depend on the temperature selected as will be apparent to one skilled in this art. Preferably hold time at these temperatures is no more than that required to produce the melt, following which the reaction mixture is immediately cooled to recrystallize pentachloronitrobenzene containing not more than 0.6% hexachlorobenzene.

EXAMPLES

In Examples 1-3 below, 123 gallons of pentachlorobenzene were added to a stirred 500 gallon reactor at 130° C. Temperature was adjusted to reaction temperatures specified below and 235 gallons of mixed acid having 17-19 wt. % $HNO_3$ and providing about 1.6 moles of $HNO_3$ per mole of pentachlorobenzene were added. Following addition, heating was commenced and continued until a liquid melt had been attained (approximately 146° C in each instance). The reaction mixture was then cooled with water through an external cooling jacket to about 50° C, filtered and product washed and dried.

EXAMPLE 1

High Temperature Addition With Rapid Heat-Up

The mixed acid was added over a period of 1.5 hours at a rate sufficient to maintain temperature at about 130° C. An additional mix time of 1.5 hours was provided prior to commencing heating to assure completion of the reaction. The reaction mixture was then heated to melt temperature over a period of 0.75 hour. Upon cooling and separating the solids (~100% conversion), the product analyzed 98.18% pentachloronitrobenzene, 0.78% hexachlorobenzene. In additional runs performed utilizing these conditions, the product had an average hexachlorobenzene content of about 1%.

This example demonstrates the high levels of hexachlorobenzene obtained when nitrating at 130° C with a rapid heat-up cycle.

EXAMPLE 2

Low Temperature Addition, Rapid Heat-Up

The mixed acid was added over a period of 2.6 hours at a rate sufficient to maintain reaction temperature at about 110° C. An additional 1.5 hours mix time was allowed following addition before commencing the heat-up cycle. The hexachlorobenzene content of the mixture prior to heating was 0.22% by weight. The reaction mixture was then heated to melt temperature over a period of 1.3 hours. At 140°-142° C, the nitric acid concentration was slightly in excess of 1% by weight of the liquid fraction. Upon cooling and separating, the solids analyzed 98.60% pentachloronitrobenzene, 0.86% hexachlorobenzene.

This example demonstrates that low temperature addition alone does not reduce hexachlorobenzene to the required levels.

EXAMPLE 3

Two runs (A and B) were made in which mixed acid was added at a rate sufficient to maintain temperature at about 110° C. Addition for Run A required 2.75 hours, for Run B, 3.5 hours. Hexachlorobenzene content following addition was 0.21 wt. % (Run A) and 0.42 wt. % (Run B). The reaction mixture was then heated slowly to melt temperature. At 140°-142° C, nitric acid concentration was 0.6 wt. % (A) and 0.34 wt. % (B). Following the melt cycle, the product (~100% conversion) of Run A analyzed 99.36% pentachloronitrobenzene, 0.36% hexachlorobenzene and the product of Run B, 99.24% pentachloronitrobenzene, 0.52% hexachlorobenzene.

This example demonstrates the necessity for low temperature addition followed by nitric acid depletion prior to reaching the melt point as claimed herein.

We claim:

1. A process for preparing pentachloronitrobenzene having reduced hexachlorobenzene content comprising the steps of:
   1. mixing together at an initial reaction temperature in the range of 100°-120° C pentachlorobenzene and a mixed nitration acid consisting essentially of sulfuric and excess nitric acid,
   2. Heating the resulting reaction mixture to an intermediate temperature in the range of 130° C up to the melt point of pentachloronitrobenzene and maintaining the reaction mixture at a temperature in said range for a period sufficient to deplete the nitric acid concentration thereof to a value of not more than 1% by weight based on the liquid fraction of the resulting slurry,
   3. Thereafter heating the resulting slurry to a temperature in the range of 142° to 160° C to form a melt and then cooling the melt to recrystallize pentachlorobenzene containing not more than 0.6% hexachlorobenzene.

2. The process of claim 1 wherein said mixed acid contains sufficient nitric acid to provide from 1.25-2 moles of nitric acid per mole of pentachlorobenzene.

3. The process of claim 2 wherein said mixed acid contains 12.5-25% by weight nitric acid.

4. The process of claim 1 wherein said initial temperature is in the range of 105°-115° C.

5. The process of claim 1 wherein said nitric acid is depleted to a value of not more than 0.8% by weight while being maintained at said intermediate temperature range but prior to exceeding a temperature of 138° C.

6. The process of claim 5 wherein said mixed acid contains 15-20% by weight nitric acid and wherein sufficient mixed acid is added to pentachlorobenzene to provide 1.4-2 moles of nitric acid per mole of pentachlorobenzene.

7. The process of claim 6 wherein said initial temperature is in the range of 105°-115° C and said intermediate temperature is in the range of 132°-138° C.

* * * * *